United States Patent [19]

Kumazawa et al.

[11] Patent Number: 5,000,843
[45] Date of Patent: Mar. 19, 1991

[54] CULTURE FLUID CONCENTRATOR

[75] Inventors: Eitaro Kumazawa, Oyama; Takao Hatai, Utsunomiya; Seiji Ishida, Ishibashi; Atushi Baba, Ishibashi; Masahiko Takahashi, Ishibashi, all of Japan

[73] Assignee: Snow Brand Milk Products Co., Ltd., Hokkaido, Japan

[21] Appl. No.: 417,472

[22] Filed: Oct. 5, 1989

[30] Foreign Application Priority Data

Oct. 17, 1988 [JP] Japan .................. 63-261056

[51] Int. Cl.⁵ ............... B01D 63/00; B01D 35/00
[52] U.S. Cl. ........................... 210/86; 210/94;
210/128; 210/195.2; 210/257.2; 210/295;
210/321.6; 210/323.1; 210/335; 73/314;
73/323; 435/286; 435/311
[58] Field of Search ............... 210/86, 94, 95, 128,
210/195.2, 257.2, 295, 321.6, 323.1, 335;
435/286, 311, 284; 73/305, 309, 314, 323

[56] References Cited

U.S. PATENT DOCUMENTS

| 2,554,100 | 5/1951 | Facchini | 73/323 |
| 2,732,715 | 1/1956 | Hawkins | 73/323 |
| 4,673,650 | 6/1987 | William I | 435/286 |
| 4,722,902 | 2/1988 | Harm et al. | 435/311 |
| 4,725,548 | 2/1988 | Karrer | 435/311 |

FOREIGN PATENT DOCUMENTS 60-137280 7/1985 Japan .
61-199788 9/1986 Japan .

Primary Examiner—W. Gary Jones
Attorney, Agent, or Firm—Griffin, Branigan & Butler

[57] ABSTRACT

There is provided between a concentrate tank and a membrane filter a circulating line which consists of a feed line and a return line. It is also possible to use an ultrafilter as the membrane filter. There is provided a leveling tube connected by respective pipes to the concentrate tank at top and bottom portions thereof, respectively. A buoy floats within the leveling tube and a position of this buoy is detected by means of transparency of the leveling tube itself or photosensors in order to detect a degree of concentration of the culture fluid progressing within the concentrate tank. There may be provided multi-stage circulating lines each connecting the associated concentrate tank to the associated membrane filter so that the culture fluid can be transferred during the process of concentration from the stage of the largest volume treatment to the state of the least volume treatment in order to concentrate the culture fluid more efficiently.

7 Claims, 2 Drawing Sheets

CULTURE FLUID CONCENTRATOR

BACKGROUND OF THE INVENTION

The present invention relates to a culture fluid concentrator used to concentrate a culture fluid cultivated previously which contains therein a specific useful substance such as physiologically active substance which has been produced by cells in a culture tank. Concentrated culture fluid is fed to a subsequent stage for extraction of said specific useful substance.

In general, production of specific useful substance by cell culture or microbe culture begins with growth of cells of microbes, then the specific useful substance is produced by these cells, followed by recovery and concentration of culture fluid, extraction of said specific useful substance, and further various stages such as decoloration and crystallization.

Presently adopted process for production of TRA (Human Tissue Plasminogen) or EPO (Erythropoietin) utilizing gene recombinant cells relies on such complicated process as mentioned above.

In such production process, an amount of the specific useful substance produced in a culture fluid is typically in the order of several mg/ml and subsequent stages to extraction of the specific useful substance from a culture fluid practically have relied on manual operation. Under the existing circumstances, only cultivation of cells and extraction of the specific useful substance have been mechanized.

Particularly in connection with the present invention, Japanese Disclosure Gazette No. 60(1985)-137280 discloses a technique according to a cell residual remover tank which is connected to a concentrator tank for cell products to effect a preliminary concentration by pressurization, decompression and circulation. A circulating continuous cultivation is also disclosed, by which culture fluid fed from a culture tank flows through a cell residual remover tank into a culture concentrating section, then added with a quantity of fresh culture ground and fed back again to the culture tank.

Japanese Disclosure Gazette No. 1986-199788 discloses a method for separation and concentration of microbe-produced substances utilizing hydrophobic porous membrane.

The culture fluid containing specific useful substance by cultivation in a culture tank usually contains therein, in addition to a large quantity of water, cell debris and protein. It also contains medium ground ingredients such as inorganic salts and serum, and impurities such as certain pharmacological effect inhibitors. Accordingly, the culture fluid is apt to be contaminated with microbes and various germs. Furthermore, the high protein concentration of culture fluid often causes bubble formation in various stages of treatment.

Particularly when protein secretion from cells occurs due to gene recombination, said protein concentration of the culture fluid necessarily increases and thus said phenomenon of bubble formation is inevitable. Though such culture fluid can be industrially produced with a productivity as high as several hundred liters per batch, efficient treatment of such large quantity of culture fluid has been impossible due to a limited filter area, when the conventional equipment for removal of impurities and for concentration of culture fluid is used to extract the specific useful substance from such a culture fluid, When the concentrator tank is made of metallic material having no transparency, level detecting electrodes may be provided within the concentrator tank to monitor concentrate level. However, such electrodes have often malfunctioned due to bubbles formed within the tank and prevented the concentrator from being smoothly operated. Additionally, it has been difficult to wash said electrodes. The electrodes sometimes require manual washing which might result in loss of air-tightness being essential for concentrating system and cause contamination of the system components.

Particularly when said contamination is due to microbes or the like, the specific useful substance would be deactivated, correspondingly increasing the pharmacological inhibitors. The inventor has found that the contamination of the concentrating system with sundry germs or the like during production of EPO makes increase of pyrogen which is exothermic substance. A molecular weight of this pyrogen is so approximate to that of the specific useful substance that the pyrogen concentration increases as the specific useful substance concentration increases during a process of membrane concentration. In view of a fact that such pyrogen occurs various inhibiting actions, it is important to avoid such increase of pyrogen. To this end, it is essential to improve air-tightness of the concentrator system.

SUMMARY OF THE INVENTION

Accordingly, a principal object of this invention is to provide a culture fluid concentrator improved so as to remove impurities from the culture fluid efficiently by use of membrane, to maintain air-tightness within the concentrator and to detect accurate progress of desired concentration.

This object is achieved, in accordance with this invention, by use of a culture fluid concentrator comprising a concentrate tank, a membrane filter connected by a line to said concentrate tank, a leveling tube connected via respective pipes to top and bottom portions of the concentrate tank, a buoy floating within said leveling tube and means to detect a position of said buoy so that concentration of the culture fluid progressing within the concentrate tank may be detected and thereby a process of concentration may be monitored.

With such arrangement, a level of the concentrate tank can be easily detected, no bubble formation occurs within the concentrate tank and accordingly no malfunction for level detection occurs as has been inevitably encounted by the case utilizing the electrodes for level detection. Particularly the arrangement that the concentrate tank is connected by the line to the membrane filter and the leveling tube is connected to the concentrate tank assures that the airtightness is maintained within the circulating line and this circulating line is protected from contamination with external microbes or the like even when the interior of said circulating line is rinsed out. With a consequence, it is possible to prevent the inhibitors from increasing in the specific useful substance during concentration within the circulating line.

Accordingly to this invention, a line branched from the line connecting the concentrate tank to the membrane filter may be connected in fluid communication to the leveling tube in order to improve the efficiency with which the leveling tube can be rinsed out.

Also according to this invention, the circulating line connecting the concentrate tank to the membrane filter may be provided in multistage fashion and thereby the culture fluid may be transferred from treatment stage of larger volume to treatment stage for smaller volume not only to improve the concentration efficiency of culture fluid but also to reduce final volume of concentrate to be concentrated along the circulating line.

BRIEF DESCRIPTION OF THE DRAWINGS

The above and other objects of the invention will be seen by reference to the description taken in connection with the accompanying drawings, in which.

DETAILED DESCRIPTION OF THE INVENTION

The present invention will be described by way of example in reference with the accompanying drawing.

Figure 1:
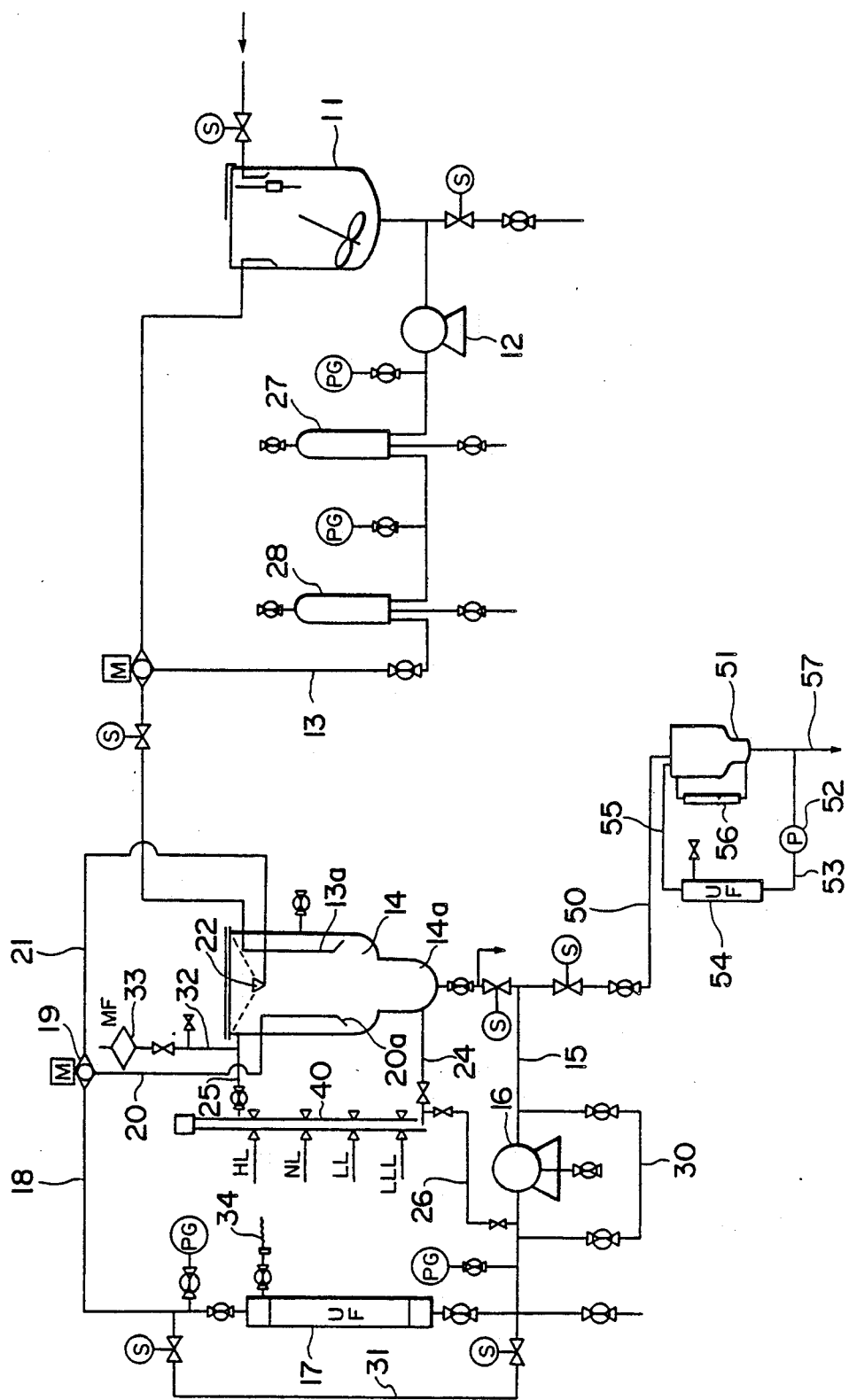
FIG. 1 is a diagram illustrating an embodiment of a process of culture fluid concentration, in which (PG) represents a pressure gauge, (M) represents a motor value and (S) represents a solenoid valve.

FIG. 1 illustrates an embodiment of the culture fluid concentrator constructed in accordance with the present invention.

The culture fluid cultivated by a culture tank (not shown) and containing a specific useful substance such as a physiologically active substance or the like having been produced therefrom is fed by a pump 12 from an intermediate tank 11 into a pipe 13. In this pipe 13, the culture fluid passes through filters 27, 28 of 10 μm to 0.22 μm adapted to remove microbes and impurities from the culture fluid, and are thereafter stored in a concentrate tank 14.

Within the concentrate tank 14, an end 13a of the pipe 13 is outwardly oriented adjacent the inner wall of the concentrate tank 14 so as to avoid bubble formation of the culture fluid as the latter is fed into the concentrate tank 14.

A bottom portion 14a of the concentrate tank 14 has a diameter smaller than that of a top portion thereof so that the culture fluid may be continuously fed to the subsequent stage even when a quantity of the culture fluid is reduced within the concentrate tank 14 and any gas may be effectively prevented from being sucked by the pump.

The culture fluid stored in the concentrate tank 14 is concentrated in a circulating line connecting the concentrate tank 14 to an ultrafilter 17. The circulating line consists of a feed line and a return line. Along the feed line, the culture fluid is fed by a pump 16 from a pipe 15 to the ultrafilter 17. After concentration by the ultrafilter 17, along the return line, the culture fluid flows out from the ultrafilter 17, then flows through a pipe 18 and a switching valve 19, and returns to the concentrate tank 14 through a pipe 20. In this manner, the culture fluid is concentrated as flowing through the circulating line consisting of the feed line and the return line.

The line switching valve 19 is adapted, during washing of the concentrate tank 14, to be switched so that the culture fluid may be fed from the pipe 21 into the concentrate tank 14. An end 20a of the pipe 20 located within the concentrate tank 14 is outwardly oriented adjacent the inner wall of the concentrate tank 14 in the same manner as in the case of the end 13a in order to avoid bubble formation of the culture fluid.

The culture fluid circulating line is provided between the concentrate tank 14 and the ultrafilter 17 in the embodiment as has been mentioned above, because, in view of a fact that the culture fluid is usually moved at a predetermined or higher flowing velocity, thereby establishing a relatively high linear velocity to prevent membrane of the ultrafilter 17 from being choked with cell debris or the like and a transmissivity of the culture fluid itself is as low as providing only an efficiency of 20 to 30 liters per hour, for example, to concentrate 50 liters of culture fluid, said circulating line must be employed and thereby the culture fluid which has been concentrated by the ultrafilter 17 must be further circulated. A cut off molecular weight of the ultrafilter 17 is in order of 10,000.

A culture fluid concentrating efficiency can be adjusted by changing the membrane area and/or the membrane configuration of the ultrafilter 17.

The ultrafilter 17 may be replaced by a filter of higher concentrating efficiency to eliminate the above-mentioned circulating system and to allow the culture fluid to be directly fed to the subsequent state after concentrated by said filter.

Even in the circulating system as mentioned above, the germless air-tight system as in said embodiment is ideal for sterilization and washing of the culture fluid concentrator and, therefore, it is preferable that there is separately provided a line by which germicide and detergent return from the ultrafilter 17 to the concentrate tank 14.

In this embodiment, a CIP shower nozzle 22 is used to wash the concentrate tank 14. Specifically, the detergent, after stored in the intermediate tank 11, is sterilized by the filters 27, 28, then fed to the concentrate tank 14, thereafter flows through the pipe 15, the ultrafilter 17, the pipe 18, and then through a pipe 21, upon switching of the line switching valve 19, into the CIP shower nozzle 22. Thus, the interior of the concentrate tank 14 is rinsed out.

Reference numeral 40 designates a leveling tube used to detect the level of fluid within the concentrate tank 14 and this leveling tube 40 is connected between a pipe 24 connected to the concentrate tank 14 at the bottom portion thereof and a pipe 25 connected to said tank 14 at the top portion thereof.

A pipe 30 and a pipe 31 are bypass pipes adapted for relief of pressure exerted on the pump 16 and the ultrafilter 17, respectively, and thereby the pump 16 and the ultrafilter 17 are protected against possible damage due to pressure.

A bypass pipe 26 connected between the pipe 24 and the pump 16 is used to wash the leveling tube 40. More specifically, the detergent fed to the pipe 15 flows, upon opening of the valve, through the bypass pipe 26 into the leveling tube 40 and, after having washed the leveling tube 40, returns to the concentrate tank 15 via the pipe 25.

Reference numeral 33 designates a sterilizing filter exposed to the atmosphere, connected to the pipe 25 which is, in turn, connected to the leveling tube 40.

Reference numeral 34 designates a pipe to exhaust waste fluid separated by the ultrafilter 17.

The process of concentration as has been described hereinabove may be summarized as follows:

The culture fluid is fed by the pump 12 from the intermediate tank 11 to the pipe 13. In this pipe 13, the culture fluid passes through the filters 27, 28 of 10 μm to 0.22 μm adapted to remove microbes and impurities from the culture fluid and then stored in the concentrate tank 14. The culture fluid thus stored in the concentrate tank 14 is fed along the feed line from the pipe 15 to the ultrafilter 17, then flows along the return line through the pipe 18, the line switching valve 19 and the pipe 20 back to the concentrate tank 14. In this way, the culture fluid repeatedly circulates through such line and is progressively concentrated. The degree of concentration can be monitored by detecting the level within the concentrate tank 14 through observing the leveling tube 40.

The manner in which the respective components of the system constructed in accordance with this invention are rinsed out may be summarized as follows:

The detergent, after having been stored in the intermediate tank 11, is sterilized by the filters 27, 28, then fed to the concentrate tank 14, thereafter flows through the pipe 15, the ultrafilter 17, the pipe 18, then, upon switching of the line switching valve 19, flows through the pipe 21 and the CIP shower nozzle 22 into the concentrate tank 14 to wash this. The detergent fed to the pipe 15 can be fed, upon opening of the valve, through the bypass pipe 26 into the leveling tube 40 and, after the latter has been washed, fed back to the concentrate tank 14 through the pipe 25.

Thus, the CIP of this invention can be achieved under the air-tight condition without any troublesome manual operation of washing as has conventionally been required, so it is assured to maintain the air-tightness within said CIP line.

The ultrafilter 17 not adapted for heat sterilization utilized chlorine as germicide and the same line as that associated with the concentrate tank 14 as well as associated with the leveling tube 40.

Figure 2:
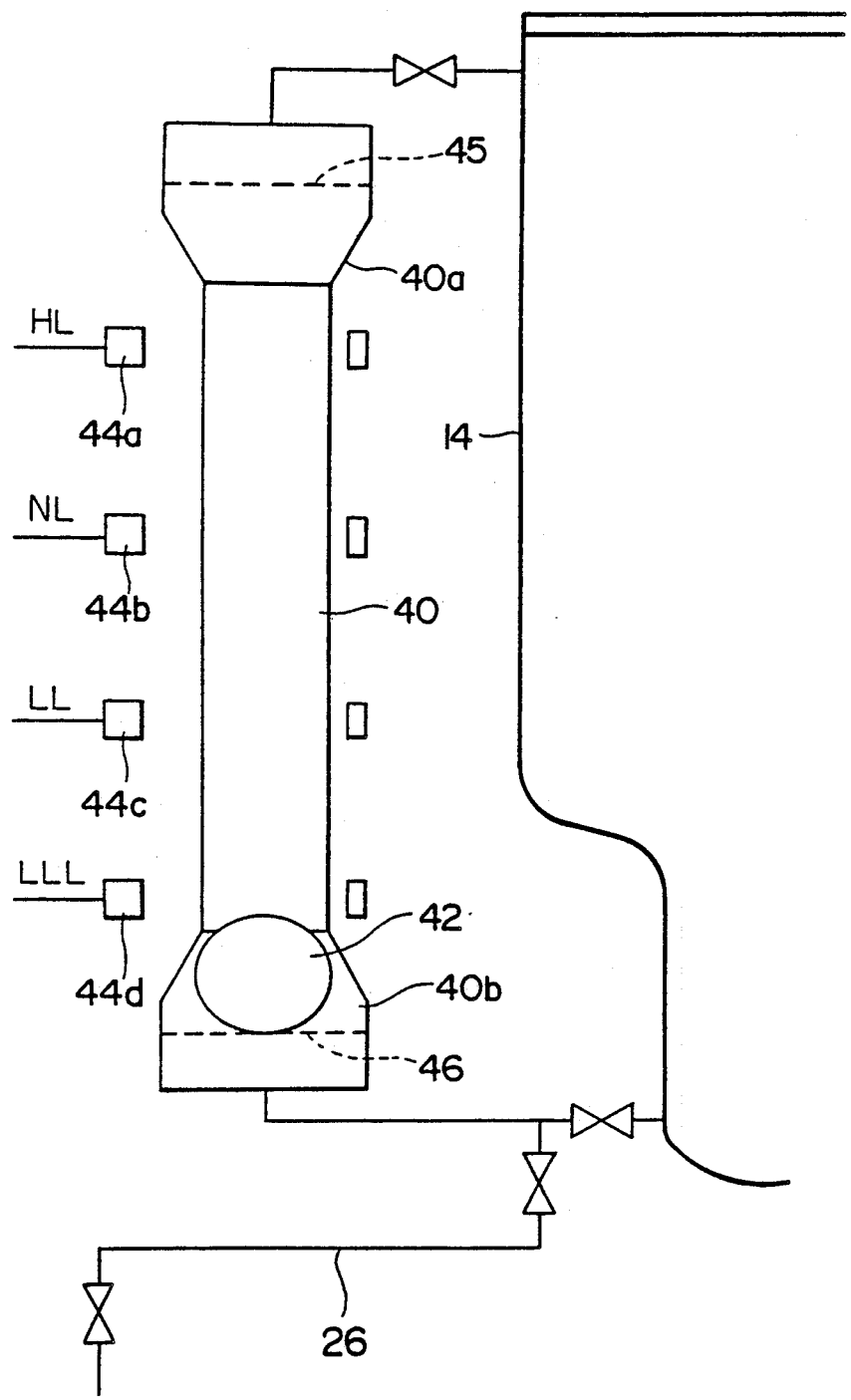
FIG. 2 schematically illustrates an embodiment of the leveling tube provided in association with a culture fluid concentrate tank to detect a level of concentrate within said tank according to the present invention.

FIG. 2 illustrates an embodiment of the leveling tube 40 used in the culture fluid concentrator of this invention. The leveling tube 40 is transparent and includes diameter-enlarged upper and lower portions 40a, 40b, respectively. A buoy 42 floats therewithin so as to follow the fluid level within the tube 40 in vertical direction. To detect a position of the buoy 42, there are provided along the length of the leveling tube 40 a series of photosensors 44a, 44b, 44c, 44d. It should be understood that 44a designates the high level sensor, 44b the neutral level sensor, 44c the low level sensor and 44d the least low level sensor. These photo-sensors are preferably displaceable.

The diameter-enlarged portions 40a, 40b of the leveling tube 40 are dimensioned so that the culture fluid may freely flow through a passage defined around the buoy 42, and these diameter-enlarged portions 40a, 40b are provided with filters 45, 46, respectively, so as to limit a movement of the buoy 42 therebetween.

Such leveling tube 40 allows the position of the buoy 42 to be detected by the photosensors and the degree of concentration progressing within the concentrate tank 14 to be easily detected.

With the above-mentioned embodiment of the concentrator adapted to concentrate the culture fluid in the circulating system, the concentration becomes bulky in proportion to the volume of culture fluid to be treated and even if the circulating volume of the culture fluid can be minimized as a result of concentration by the ultrafilter, the final volume of concentrate is still as large as several liters to ten-odd liters. To overcome such limitation, there may be provided an additional concentrator which is scaled down with respect to the main concentrator including the concentrate tank 14 for further concentration to be a final volume in order of one liter.

FIG. 1 shows in a portion lower than a pipe 50 a second stage concentrator which is scaled down with respect to the final stage concentrator including the concentrate tank 14. The culture fluid already concentrated is fed from the first stage concentrator through the pipe 50 into a concentrate tank 51, then fed by a pump 52 through a pipe 53 into an ultrafilter 54. The culture fluid concentrated by this ultrafilter 54 is recirculated through a pipe 55 back to the concentrate tank 51. The degree of concentration progressing within the concentrate tank 51 is monitored through a leveling tube 56.

The culture fluid thus concentrated by the ultrafilter 54 will be supplied through a pipe 57 into a column for extraction process (not shown) where the specific useful substance is extracted.

As will be apparent from the foregoing description, multi-stage concentration lines each comprising the concentrate tank and the ultrafilter in the form of membrane filter may be successively scaled down from the stage of the largest volume treatment to the stage of the least volume treatment in order to improve the concentrating efficiency.

In this way, the concentrator of this invention is advantageous over the prior art in that the impurities can be efficiently removed from the culture fluid, the air-tightness can be adequately maintained throughout the process of concentration and the progress of concentration can be precisely controlled.

While the invention has been particularly shown and described with reference to preferred embodiment thereof, it will be understood by those skilled in the art that the foregoing and other changes in form and details can be made therein without departing from the spirit and scope of the invention.

What is claimed is:

1. A culture fluid concentrator comprising a concentrate tank, a membrane filter connected by a circulating line to said concentrate tank, a leveling tube connected via respective pipes to top and bottom portions of the concentrate tank, a buoy floating within said leveling tube and photosensor means to detect a position of said buoy so that concentration of the culture fluid progressing within the concentrate tank may be detected and thereby a process of concentration may be monitored.

2. A culture fluid concentrator as recited in claim 1, wherein said circulating line consists of a feed line and a return line.

3. A culture fluid concentrator as recited in claim 1, wherein the leveling tube is transparent.

4. A culture fluid concentrator as recited in claim 1, wherein there is provided a line branched from the circulating line connecting the concentrate tank to the membrane filter and connected to the leveling tube wherein a wash liquid may be passed through the leveling tube to maintain sanitary conditions in the leveling tube and avoid pyrogen increases.

5. A culture fluid concentrator as recited in claim 1, wherein there is provided a line branched from a return line of the circulating line which return line extends from the membrane filter to the concentrate tank and the branched line is connected to a shower provided in the top portion of the concentrate tank.

6. A culture fluid concentrator as recited in claim 1, wherein there are a plurality of multi-stage circulating lines, each of which respectively connect one of a plurality of associated concentrate tanks to one of a plurality of associated membrane filters so that the culture fluid may be transferred during the process of concentration from a stage of the largest volume treatment to a stage of the least volume treatment.

7. A culture fluid concentrator as recited in claim 1, wherein the membrane filter utilizes an ultrafilter.

* * * * *